United States Patent [19]

Dasgupta

[11] Patent Number: 4,920,056

[45] Date of Patent: Apr. 24, 1990

[54] APPARATUS AND METHOD FOR AUTOMATED MICROBATCH REACTION

[75] Inventor: Purnendu K. Dasgupta, Lubbock, Tex.

[73] Assignee: The Dow Chemical Company, Midland, Mich.

[21] Appl. No.: 158,181

[22] Filed: Feb. 19, 1988

[51] Int. Cl.$^5$ .................... G01N 35/00; G01N 31/16
[52] U.S. Cl. ........................................ 436/50; 436/51; 436/43; 422/75; 422/76; 422/81; 422/82; 422/130
[58] Field of Search .................... 422/62, 63, 67, 75, 422/76, 81, 82, 130, 100; 436/43, 50, 51, 148, 150, 180, 89

[56] References Cited

U.S. PATENT DOCUMENTS

| | | | |
|---|---|---|---|
| 3,488,154 | 1/1970 | Hronas | 422/81 X |
| 3,654,113 | 4/1972 | Bochinski | 422/81 X |
| 3,725,010 | 4/1973 | Penhasi | 436/89 X |
| 4,003,705 | 1/1977 | Buzza et al. | 436/133 X |
| 4,022,575 | 5/1977 | Hansen et al. | 436/52 |
| 4,042,326 | 8/1977 | Kallos | 436/126 |
| 4,116,046 | 9/1978 | Stein | 73/61.1 C |
| 4,436,822 | 3/1984 | Eseifan | 422/63 X |
| 4,615,866 | 10/1986 | Hyde et al. | 436/43 X |

OTHER PUBLICATIONS

James K. Foreman and Peter B. Stockwell, Automatic Chemical Analysis, (Sussex, England: Ellis Horwood Limited, 1975), pp. 96–114.

Leonard T. Skeggs, Jr., Ph.D., "An Automatic Method for Colorimetric Analysis," Am. J. Clin. Pathol., vol. 28, 1957, pp. 311–322.

Douglas A. Skoog, Principles of Instrumental Analysis, 3rd Edition, (Saunders College Publishing), "Automated Methods of Analysis," pp. 851, 872–873, 1985.

R. L. Habig, B. W. Schlein, L. Walters and R. E. Thiers, "A Bubble-Gating Flow Cell for Continuous-- flow Analysis," Clin. Chem., vol. 15, 1969, pp. 1045–1055.

Purnendu K. Dasgupta, Jae-Seong Rhee and Ellis L. Loree, "A Simple and Versatile Photodetector System for Peak Width Measurement-Based Flow Injection Analysis," Spectroscopy, vol. 2, No. 10, 1987, pp. 39–43.

Hoon Hwang and Purnendu K. Dasgupta, "Fluorometric Flow Injection Determination of Aqueous Peroxides at Nanomolar Level Using Membrane Reactors," Analytical Chemistry, vol. 58, No. 7, Jun. 1986, pp. 1521–1524.

K. J. Clevett, Process Analyzer Technology, (New York: Wiley, 1986), pp. 588–600.

Primary Examiner—Michael S. Marcus
Assistant Examiner—D. John Griffith, Jr.
Attorney, Agent, or Firm—Timothy S. Stevens; Burke M. Halldorson

[57] ABSTRACT

Apparatus and method for automatic microbatch reaction including a reactor having a reaction chamber, such as a 1.5 milliliter plastic centrifuge tube having a conical bottom. An automatically actuated injection valve is used to inject less than 1 milliliter of a sample into the reaction chamber. One or more automatically actuated reagent valves are used to introduce respective pressurized reagents into the reaction chamber to process the sample. The volume of the reagent(s) introduced into the reaction chamber is less than 1 milliliter and controlled by the on time of the respective reagent valve. The automatically actuated valves are controlled by a computer based timer. A sensor positioned in the chamber, such as a pH electrode, can be used to analyze the processed sample in place or the processed sample can be analyzed by flowing it from the reaction chamber through a flow-through detector, such as a flow-through spectrophotometer.

17 Claims, 3 Drawing Sheets

APPARATUS AND METHOD FOR AUTOMATED MICROBATCH REACTION

FIELD OF THE INVENTION

The present invention is in the field of chemical analysis and more specifically in the field of apparatus and methods for automated chemical analysis of liquid samples.

BACKGROUND OF THE INVENTION

As the number of samples to be analyzed continue their ever increasing pattern, the importance of automated chemical analysis procedures continues to increase as well. So far for liquid-phase analysis, the major emphasis has been on continuous flow systems. Segmented Continuous Flow Analysis (SCFA) as introduced by Skeggs in 1957 (*Am. J. Clin. Pathol.*, 28, pp. 311-322) was commercialized subsequently by the Technicon Corporation and proved so extraordinarily successful that for years automated liquid-phase analysis was synonymous with the trade name of the Technicon instrument, the Autoanalyzer. More recently, Flow Injection Analysis (FIA), also a continuous flow procedure but without segmentation, has proved to be a formidable contender to SCFA (see U.S. Pat. No. 4,022,575 to Hansen and Ruzicka). Despite the unique ability of FIA to provide reproducible dispersion profiles, the overwhelming majority of FIA applications continue to involve single-point measurement (typically peak height). In such a case, FIA is merely an analog of SCFA.

Liquid-phase analysis can be automated without continuous flow. One example of this is represented by the DigiChem 4000 series analyzer marketed by Ionics, Inc. In this analyzer, the sample and up to five reagents are delivered to a reaction cell by steppermotor driven syringes The contents of the cell are then mixed by spinning the cell. Higher speed spinning is used to empty the cell after in-situ detection, e.g., by placing a pH probe in the cell. Although a volumetric resolution of 0.12 microliter is possible with small volume syringes, the total measurement volume must be much higher overall, it cannot be considered a microscale analyzer. However, the concept is sufficiently unique and the potential sufficiently diverse that the instrument is now discussed in textbooks such as "Process Analyzer Technology" published by Wiley in New York in 1986 and authored by K. J. Clevett as well as "Principles of Instrumental Analysis", 3rd edition, published by Saunders in New York in 1985 and authored by D. A. Skoog.

In addition, Kallos, in U.S. Pat. No. 4,042,326, describes an automated batch analysis system where a volume of sample and a volume of reagent (or reagents) are added to a reaction chamber to form a reaction product that is subsequently analyzed. The system of Kallos also cannot be considered a microscale analyzer. Some clinical type analyzers (such as the ones described in "Automatic Chemical Analysis" published by Horwood in Sussex, England in 1975 and authored by Foreman et al.) can be considered microscale systems but so far do not find much use in non-clinical laboratories, probably because they are complex and costly systems, e.g., they generally use many test tube-like reaction chambers and transport the chambers from station to station to receive samples and reagents.

SUMMARY OF THE INVENTION

The present invention is a new alternative to perform batch-mode liquid-phase reactions for chemical analysis on a microscale and can be practiced using less complex and expensive equipment. In one embodiment, the invention is an apparatus for automatic microbatch reaction. The apparatus comprises a reactor which defines a reaction chamber, such as a plastic centrifuge tube having a conical bottom. An automatic liquid sample injection valve, such as an automatic liquid chromatography injection valve, is in fluid communication with the reaction chamber. An automatic liquid reagent valve, such as an on/off microsolenoid valve, is also in fluid communication with the reaction chamber and a pressurizable liquid reagent reservoir is in fluid communication with the reagent valve. An automatic control means, such as a programmable electronic timer, is used to automatically control the injection and reagent valves in a programmed sequence. This structure allows a preselected microvolume of a sample to be flowed into the reaction chamber and allows the flowing of a microvolume of a liquid reagent contained in the reagent reservoir to be flowed for a controlled length of time through the reagent valve into the reaction chamber. The sample and the reagent can then react with each other in the reaction chamber. The analysis can be completed by flowing the reaction products to a detector, such as a flow-through photometric detector. An alternative way of completing the analysis is to expose a sensor to the contents of the reaction chamber so that the sample can be titrated by the reagent or so that a reaction product of the sample and the reagent can be determined. The sensor can be a potentiometric probe (such as a pH electrode), a conductimetric probe (such as a pair of spaced apart wires exposed to the reaction chamber), an amperometric probe (such as a platinum electrode/mercury electrode/reference electrode exposed to the reaction chamber), and a photometric probe (such as a fiber optic probe or even a photometric sensing system comprising simply a beam of light directed through the reaction chamber).

In another embodiment, the present invention is a method for automatic microbatch reaction comprising at least two steps. The first step is to automatically flow a preselected microvolume of a liquid sample into a reaction chamber. The second step is to automatically flow a microvolume of a liquid reagent into the reaction chamber for a controlled length of time so that a component of the sample can react with a component of the reagent to produce a reaction product. The analysis can be completed by the additional step of determining the concentration of an analyte in the reaction chamber. The analyte can be a component of the sample (such as hydrogen ion, determined by a pH electrode positioned in the reaction chamber), a component of the reagent (such as hydrogen ion, determined by a pH electrode positioned in the reaction chamber) and a reaction product between a component of the sample and a component of the reagent (such as the blue complex formed between ammonia and copper ion determined by a photometric system comprising a photometric probe positioned in the reaction chamber). The step of automatically flowing a microvolume of a liquid reagent into the reaction chamber for a controlled length of time so that a component of the sample can react with a component of the reagent to produce a reaction product can be repeated in a discrete or continuous fashion so that more reagent can be added to the reaction chamber to, for example, discretely or continuously titrate a sample.

DETAILED DESCRIPTION OF THE INVENTION

Figure 1:
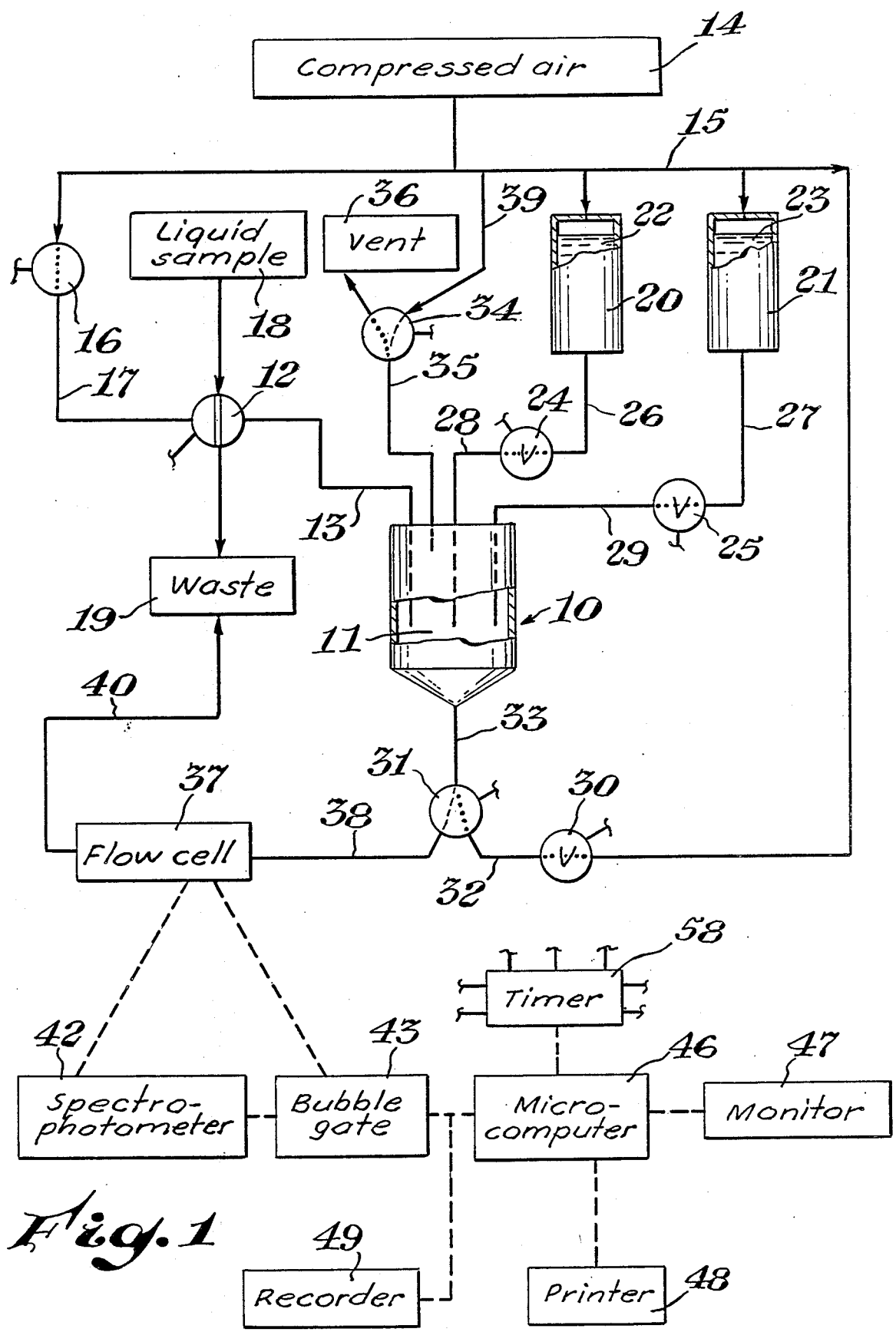
FIG. 1 is a schematic drawing of an apparatus embodiment of the present invention.
Figure 2:
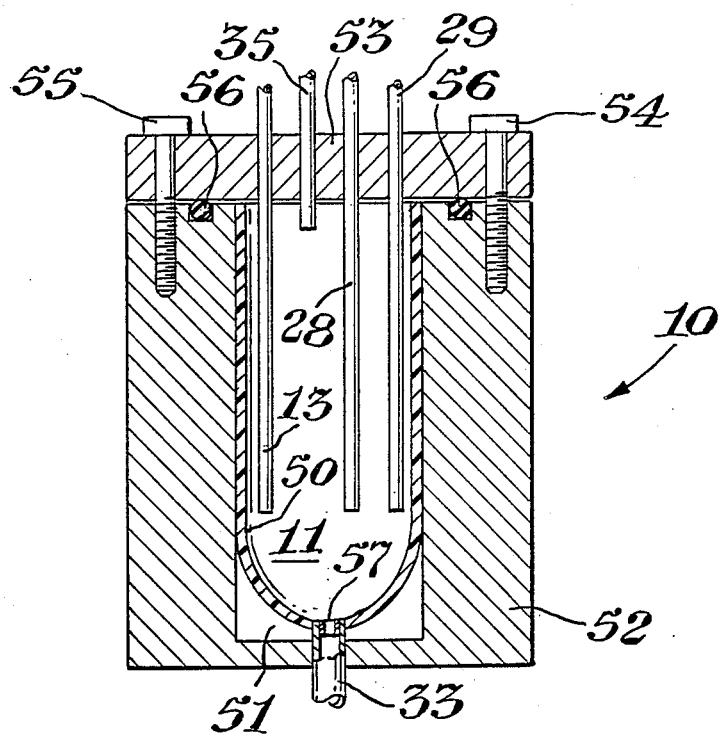
FIG. 2 is a side view, mostly in section and partly in full, of a reactor embodiment according to the present invention showing a short section of glass tubing inserted in the end of the tubing leading from the bottom of the chamber of the reactor.

Referring now to FIG. 1, therein is shown a schematic drawing of an apparatus embodiment of the present invention including a reactor 10 defining a reaction chamber 11. FIG. 2 is a side view, mostly in section and partly in full, of the reactor 10. An automatic liquid sample injection valve 12 is shown in fluid communication with the chamber 11 by tubing 13. A source of compressed air 14 is shown in fluid communication with a tubing manifold 15. The manifold 15 is shown in fluid communication with an automatic on/off valve 16. The valve 16 is shown in fluid communication with the injection valve 12 by tubing 17. The dotted line shown through the valve 16 is meant to depict the flow path when the valve 16 is automatically placed in the "on" position to allow flow through it. When the valve 16 is in the "off" position, there is no flow through the valve 16, of course. The injection valve 12 is schematically shown in the "load" position so that a liquid sample can flow through the valve 12 to waste 19. When the valve 12 is automatically placed in the "inject" position and the valve 16 is automatically placed in the "on" position, a microvolume of the sample 18 in the valve 12 is blown by compressed air through the tubing 13 into the chamber 11. The term "microvolume" here and in the claims means less than 1 milliliter. Frequently, the injection volume is less than 0.1 milliliter. It should be understood that the means used to move the sample from the sample injection valve to the chamber is not critical to the present invention and that this can be done by a flowing stream of liquid.

FIG. 1 also shows two pressurized liquid reagent reservoirs 20 and 21 filled with liquid reagents 22 and 23. Although two reagent reservoirs are shown in FIG. 1, any number can be used, of course, and they can be pressurized by means other than pneumatic means, such as a pump. The top of the reservoirs 20 and 21 are shown in fluid communication with the manifold 15 so that the reagents 22 and 23 are pressurized. Two automatic on/off valves 24 and 25 are shown in fluid communication with the bottom of the reservoirs 20 and 21 by tubing 26 and 27. The valves 24 and 25 are shown in fluid communication with the chamber 11 by tubing 28 and 29. Automatically turning "on" either of the valves 24 or 25 thus results in flow of a liquid reagent into the chamber 11 for as long a time as the valves are in the "on" position but not so long that more than a "microvolume" is delivered, i.e., no more than 1 milliliter. The flow rate of reagent depends primarily on the reagent pressure, the reagent viscosity and the dimensions of the tubing 28 and 29 as is well understood by the art. Another automatic on/off valve 30 is shown in fluid communication with the manifold 15. The valve 30 is shown in fluid communication with a three-way valve 31 by tubing 32. The flow pattern through the valve 31 is shown either along the dotted line or the dashed line. When the valve 31 is in the dotted line position and the valve 30 is in the "on" position, compressed air can flow through the valves 30 and 31 into the chamber by way of tubing 33. If there is any liquid in the chamber 11, this air can bubble through it to mix the liquid. Another automatic tree-way valve 34 is shown in fluid communication with the chamber 11 by tubing 35. When the valve 34 is in the dotted line position, the air entering the chamber 11 from tubing 33 can flow through the tubing 35, through the valve 34 to vent 36. The valve 31 is also shown in fluid communication with a flow cell 37 by tubing 38. When the valves 31 and 34 are placed in the dashed line position, compressed air can flow through a tube 39, through the valve 34, through the tube 35 to the chamber 11. If there is liquid in the chamber 11, it is thus forced through the tube 33, through the valve 31, through the tube 38, through the flow cell 37 to waste 19 through a tube 40.

Figure 3:
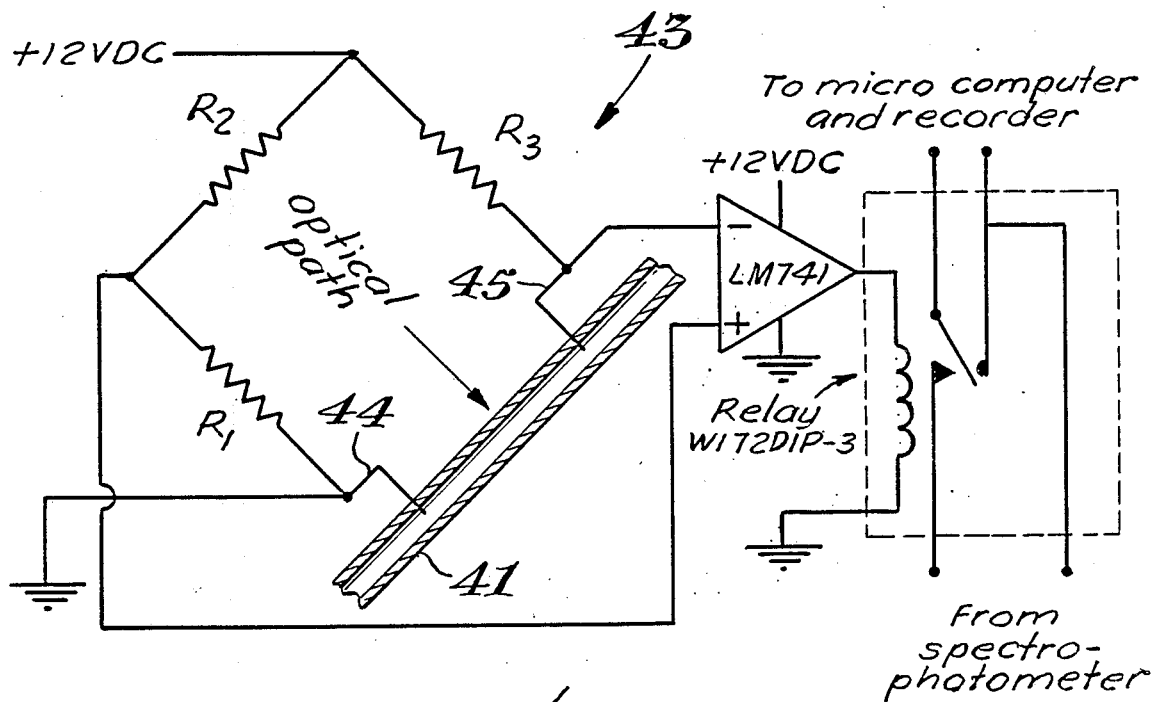
FIG. 3 is an electrical circuit drawing of the bubble gate shown schematically in FIG. 1.

The flow cell 37 includes a section of 1.65 mm inside diameter glass tubing 41 shown in section in FIG. 3 The remainder of the flow cell 37 and the spectrophotometer 42 is not shown in detail but will be described now. The optical path through the tubing 41 is the radial dimension: a small tungsten lamp powered by a constant current source is followed by an interchangeable interference filter which permits wavelength selection and is located on one side of the tubing 41 after an appropriate aperture. A photodiode detects the transmitted light on the other side, again through an appropriate aperture. A similar system is commercially available from Jasco Inc. and further information can be had by reference to Dasgupta et al., *Spectroscopy*, 1987, 2 (10) pp. 39–43. A bubble gate 43 is shown in detail in FIG. 3 and was derived from the work of Habig et al., *Clin. Chem.*, 1969, 15, 1045–1055. A Wheatstone Bridge circuit is shown where R1 is a 5 megohm potentiometer, R2 is a 1 megohm resistor and R3 is a 1.3 megohm resistor. Two sides of the bridge are shown fed with 12 volts DC and the other two sides of the bridge are shown connected to a voltage comparison amplifier LM741 with its output governing a relay such as a W172DIP-3 relay. Wire probes 44 and 45 are shown protruding through the tubing 41 so that when there is conducting liquid between the probes 44 and 45, the signal from the spectrophotometer is allowed to go to the microcomputer 46 and the recorder 49 but when this is not true, the microcomputer/recorder inputs are short circuited. Note that formation of a thin liquid film on the tubing 41 between the probes 44 and 45 providing some conductance between the probes can occur in many cases. However, the potentiometer R1 provides a "sensitivity adjust" control which easily distinguishes between a film and a completely filled region between the probes 44 and 45. The microcomputer 46 is an Apple IIe equipped with a 12-bit A/D to read the signal ten times per second from the spectrophotometer 42 through the bubble gate 43 and display it on a monitor 47 as a continuously moving Y-time plot. Software integral to the system computes the mean and the standard deviation of the individual readings and stores the results on a magnetic disc resident in the microcomputer 46 or prints it on demand on the printer 48. The standard deviation of the readings taken on a single draining of liquid from the chamber 11 serves as a diagnostic tool and simultaneously evaluates mixing uniformity of liquids in the chamber 11, presence of any microbubbles and spectrophotometer stability. The conductivity approach shown in FIG. 3 is not likely to succeed with resistive organic liquids. Experiments show that photoemitter-detector assemblies designed for detecting changes in reflectance, e.g., type OPB125A, located outside the tube immediately before the optical path can sense the presence of a liquid slug in the tubing 41, and distinguish it from a film, because of the change in reflectance. In this case, energizing/de-energizing of the relay is delayed slightly (representing the transit time between the slug sensor and the optical path) compared to the precise time of the triggering of the sensor. It should be understood that the present invention is not limited to the use of a spectrophotometer as a detector and that almost any detector, such as an electrochemical detector, a fluorescence detector, a conductivity detector and a refractive index detector can be used.

Figure 6:
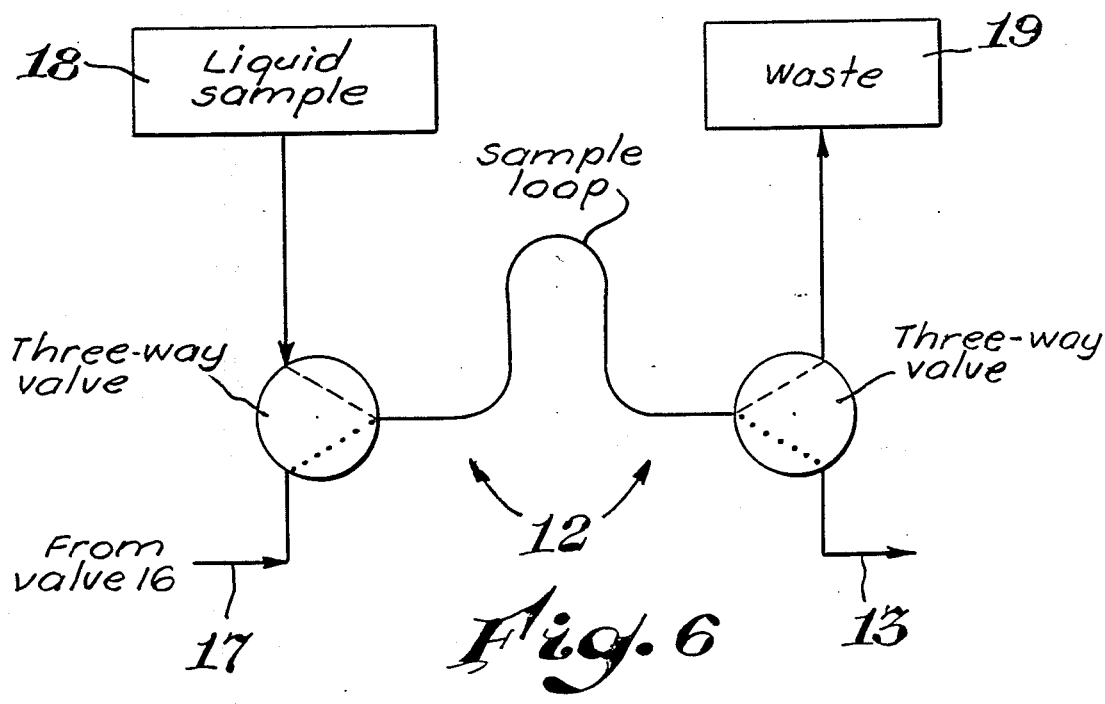
FIG. 6 is a schematic drawing of the injection valve 16 of FIG. 1 in more detail.

A timer 58 (MicroMaster LS made by Minarik Electric, Los Angeles, CA) is tied to the microcomputer 46. Together they constitute an automatic control means for automatically controlling the valves 12, 16, 24, 25, 30, 31 and 34 (the wires connecting these valves and the timer are not completely shown). The valves 16, 24, 25, and 30 are type LFAA 1200618H from The Lee Company, Westbrook, CT. The valves 34 and 31 are type LFYX 0500200AC from Lee. The specific automatic injection valve 12 used is not critical to the present invention. However, in one preferred embodiment the valve 12 is a pair of simultaneously actuated three-way valves, type 075T3WMP12-32 from Biochem Valve Corporation, East Hanover, NJ, with an injection loop between the common valve port of each valve as shown schematically in FIG. 6. All of the above valves operate on 12 volts DC and although the timer provides such voltage output, an external 12 volt DC power supply was used to prevent overloading the capacity of the timer itself. The automatic valves can be operated by any suitable means other than directly by electrical solenoids, such as by pneumatic means. In addition, if desired pressure regulators can be used in the compressed air system shown in FIG. 1 to deliver different air pressures to the different points of use, e.g., the reagent reservoirs 20 and 21 could be pressurized to different pressures if desired.

Referring now to FIG. 2, therein is shown a detailed view, mostly in section and partly in full, of the reactor 10. The reactor 10 includes a 1.5 milliliter capacity disposable polypropylene microcentrifuge tube 50 (Elkay Products, Shrewsbury, MA) with its top rim cut off and potted in epoxy resin 51 inside a cylindrical Plexiglas polymer enclosure 52. The tubes 13, 28, 29, and 35 are 0.3 mm inside diameter Teflon ® tubes, type 30 LW from Zeus Industrial Products, Raritan, NJ, and are inserted through narrow holes drilled in the cover 53. The holes in the cover 53 are drilled slightly undersized compared to the outside diameter of the tubes. To insert the tubes, the end of each tube is cut in a tapered fashion, inserted through the holes in the cover and then pulled through; an air-tight fit is thus obtained. It is important to use small internal diameter tubes 13, 28 and 29; a small exit orifice increases the terminal velocity of the delivered liquid and prevents drop adherence. This problem can also be solved by having the ends of the tubes 13, 28 and 29 dip below any liquid in the chamber 11. The cover 53 is bolted to the enclosure 52 by bolts 54 and 55, with an 0-ring gasket 56. Because the tube 50 has a hydrophobic surface, it is not wetted well by aqueous solutions. If the inside diameter of the tube 33 is relatively large, instead of small gas bubbles rising through a liquid in the chamber 11, the entire liquid layer tends to lift up and collapse. That the problem is indeed related to surface wetting is corroborated by its absence when experiments are conducted with a liquid of lower surface tension than water, e.g., methanol. The problem was effectively solved by treating the tube 50 with hot concentrated nitric acid for ten minutes as well as putting an 0.25 mm internal diameter glass capillary tube 57 at the end of the tube 33, as shown in FIG. 2, to generate small bubbles.

Figure 4:
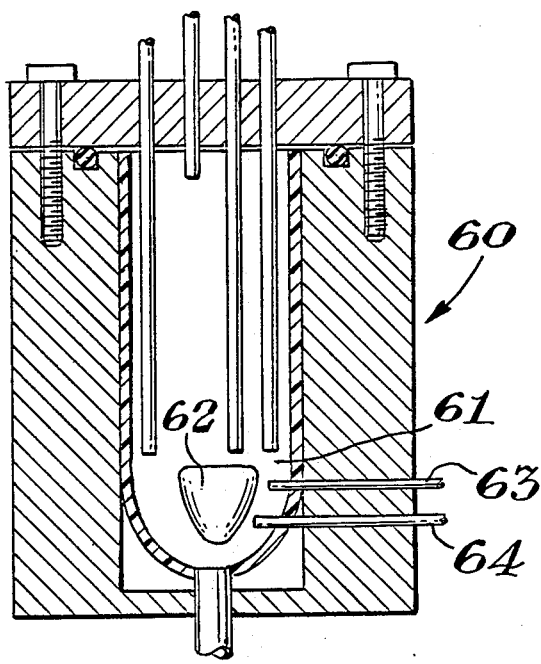
FIG. 4 is a side view, mostly in section and partly in full, of another reactor embodiment according to the present invention showing a pair of wires exposed to the chamber of the reactor.

Referring now to FIG. 4, therein is shown a side view, mostly in section and partly in full, of a another reactor embodiment 60 of the present invention. The reactor 60 defines a reaction chamber 61 and is similar to the reactor 10 shown in FIG. 2 except that the reactor 60 is shown with a magnetic stirrer 62 to mix any liquid in the chamber 61. A pair of wires 63 and 64 are shown exposed to the chamber 61 so that the electrical conductivity of a liquid in the chamber 61 can be determined.

Figure 5:
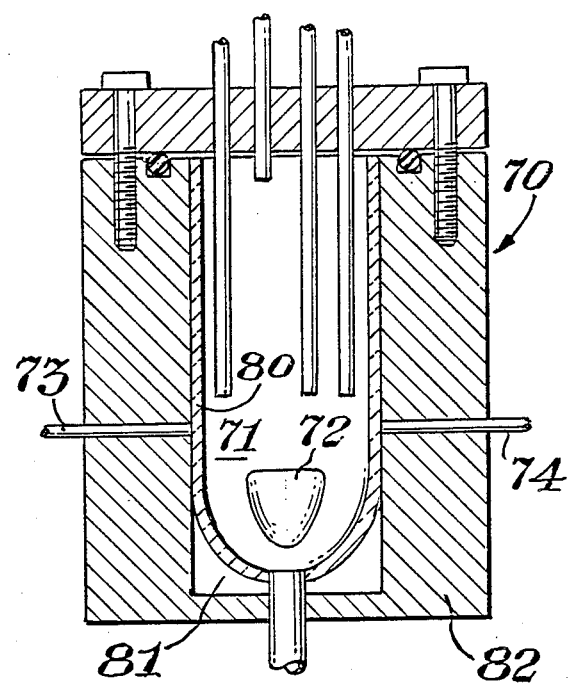
FIG. 5 is a side view, mostly in section and partly in full, of another reactor embodiment according to the present invention showing a pair of optical fibers embedded in the enclosure of the reactor.

Referring now to FIG. 5, therein is shown a side view, mostly in section and partly in full, of a another reactor embodiment 70 of the present invention. The reactor 70 defines a reaction chamber 71 and is similar to the reactor 10 shown in FIG. 2 except that the reactor 70 is shown with a magnetic stirrer 72 to mix any liquid in the chamber 71. In addition, the reactor 70 uses a glass test tube 80 potted by epoxy resin 81 in a plexiglas enclosure 82. A pair of optical fibers 73 and 74 are shown embedded in the enclosure 82 so that light can be directed down the fiber 73, shine through the chamber 71 and then be directed by fiber 74 to a photodetector.

EXAMPLE 1

The apparatus described above with regard to FIG. 1 is assembled and programmed. The injection valve 12 injects about 0.0705 milliliter of sample. The tubing 28 and 29 are each 0.3 mm internal diameter and 15 cm long. The compressed air pressure is about 6 psig. The relationship between the "on" time of either of valves 24 and 25 and the volume of aqueous reagent delivered is linear with a zero intercept (correlation coefficient of better than 0.999) for valve "on" times of 100 to 2000 milliseconds. This apparatus is used to determine copper and its blue tetramine complex by reaction with excess ammonia. Various concentrations (0–0.1 M) of copper sulfate are prepared and injected to the reaction chamber 11 along with 0.064 milliliter of 1 M ammonium hydroxide/0.05 M ammonium nitrate reagent from the reservoir 20. The system automatically mixes the sample and reagent with air and then flows the mixture through the flow cell 37. The results show a linear relationship between injected concentration and optical absorbance with a correlation coefficient of better than 0.999 and with a zero intercept. Typical relative standard deviations for replicate injections is 1.5 percent. Since the sample and the reagent react virtually instantaneously, they can be flowed to the flow cell 37 immediately after mixing in the chamber 11, allowing a sample throughput rate of 210 samples per hour. Much faster sample throughput is possible, when desired, by measuring the optical density of the mixture of sample and reagent directly in the reaction chamber 11 (as in FIG. 5). This example demonstrates a preferred mode of the invention for the determination of copper in liquid samples.

EXAMPLE 2

The apparatus of Example 1 is used except that another reagent reservoir and valve system are added for the determination of traces of ammonia in liquid samples by the nitroferricyanide catalyzed Berthelot reaction resulting in the formation of indophenol blue. The reaction involves the sequential addition of phenol/sodium nitroferricyanide, EDTA/NaOH solution and sodium hypochlorite to a sample. Since this reaction is not instantaneous, it is necessary to determine the optimum reaction time. This is accomplished by programming the valve 34 to vent the compressed air which drives the mixed liquid from the chamber 11 to the flow cell 37 when the liquid reaches the flow cell 37. The reaction is then allowed to proceed in the flow cell and after 120 seconds is complete. Approximately 0.070 milliliter of sample is injected to the chamber 11 along with about 0.055 milliliter of each reagent in sequence Carryover is measured with alternate injections of blank and a high level standard and is found to be about 4.2 percent. This is acceptable for many cases: for others, it may be necessary to wash once with the sample (and reagents) and then discard, without performing any measurement. The wash sample need not proceed to the flow cell 37: a second automatic three-way valve connected between the valve 31 and the flow cell 37 could be used to dump the wash cycle to waste 19. The tube 38 is not designed to accommodate more than one batch at a time. As a result, the sample throughput rate is inversely dependent on the necessary reaction time, as in stopped-flow FIA. It should be possible to utilize a longer length of tubing 38 to hold a number of air-separated processed samples. This example demonstrates the determination of ammonia in liquid samples.

EXAMPLE 3

The apparatus of Example 2 is changed to replace the reactor with the reactor shown in FIG. 4. The tube 38 is directly connected to the tube 40. The wires (0.5 mm diameter platinum wires) are connected to a Wescan Model 213 conductivity detector which is appropriately modified to receive this input. The output signal from the detector is transmitted directly to the recorder 49 via an electromechanical relay triggered by the timer 58. Liquid mixing in the chamber 61 is achieved by a magnetic spinbar 62 (S 8314-31, American Scientific Products) and a magnetic stirrer. The tube 28 is a 150 cm long section of 0.3 mm internal diameter Teflon ® tubing so that only about 0.00065 milliliter of reagent 22 is delivered for a valve 24 on time of 0.1 second. The injection valve 12 is adjusted to inject about 0.152 milliliter of a liquid sample of from 0–0.1 M aqueous hydrochloric acid. The reagent 22 is 0.5 M aqueous sodium hydroxide, delivered by intermittently turning on and off valve 24. The average flow rate of reagent 22 into the chamber 61 is about 0.00325 milliliter per second with a 50 percent duty cycle of the valve 34 to about 0.00031 milliliter per second with a 4.8 percent duty cycle. Replicate titrations at each delivery rate of reagent 22 show that reproducibility is improved at slower delivery rates. A delivery rate of 0.00162 milliliter per second (25 percent duty cycle) is chosen as a compromise between good reproducibility and small analysis time. The titration curves produced by the recorder 49 show the expected break in conductivity at the endpoint of the titration. A calibration curve shows a linear plot with a correlation coefficient of 0.9983 with a very small Y-intercept attributed to the finite response time of the detector. The relative standard error of the calibration slope is about 3.6 percent. This example demonstrates a microbatch titration with a conductivity probe exposed to the reaction chamber.

EXAMPLE 4

The apparatus of Example 3 is changed to replace the reactor with the reactor 70 shown in FIG. 5. The tube 28 is a 15 cm long section of 0.3 mm internal diameter Teflon ® tubing. The optical fiber 73 is used to direct light from a 660 nm red LED (0063-3061, General Fiber Optics) into the chamber 71. A portion of the light transmitted through the reaction chamber 71 is collected by the optical fiber 74 and directed to a photodiode (81-0100-3061, General Fiber Optics). The photodiode output is amplified through a Keithley Model 427 current amplifier. The signal from the amplifier is transmitted directly to the recorder 49 via an electromechanical relay triggered by the timer 58. The sample volume injected and the reagent volumes are larger so that the liquid level in the chamber 71 will rise to that of the optical fibers 73 and 74. The sample is 0–20 parts per million dodecylbenzene sulfonic acid (DBSA) in water. The reagent 22 is one liter of water containing 30 milligrams of methylene blue, 50 grams of sodium dihydrogen phosphate having one water of hydration, and 6.8 milliliters of concentrated sulfuric acid. The reagent 23 is methyl isobutyl ketone (MIBK). The valve 25 is changed to an all Teflon ® wetted surface type (075T3WMP 12-32, Biochem Valve Corp.) for solvent resistance. The injection volume is 0.120 milliliter followed by 0.465 milliliter of reagent 22 and 0.654 milliliter of reagent 23. The mixture is stirred for 30 seconds and then the stirrer is automatically turned off to let the MIBK layer float to the top in the chamber 71 over the next 5 seconds. The transmittance is then recorded for the next 5 seconds and the transmittance values translated to absorbance. The calibration plot of 0, 5, 10, 15, and 20 parts per million DBSA is linear with a correlation coefficient better than 0.999 and a relative standard error of slope of 1.9 percent. At higher concentrations of DBSA, increasingly negative deviations from linearity are observed. For replicate samples at each concentration, relative standard deviation ranged from 0.3 to 4 percent. This example demonstrates a microbatch reaction and extraction with a photometric probe exposed to the reaction chamber.

EXAMPLE 5

The apparatus of Example 4 is changed by removing the optical fibers 73 and 74 and replacing the optical fiber 73 with an optical fiber bundle made by using a 1 mm diameter silica fiber (Ensign-Bickford Optics) as a core, surrounded by a large number (approximately 100) of 0.2 mm diameter glass optical fibers (Edmond Scientific) with the end of the bundle butted against the tube 80. The integrity of the bundle was maintained for about 10 cm beyond this point by heat-shrinking a black polyethylene tube around it, resulting in a total diameter of about 2 mm. Past the first 10 cm, the silica fiber is separated from the glass fiber bundle. Light from an He-Cd laser (model 339 M) powered by a model 100 power supply (Omnichrom Inc., Chino, CA) is directed into the silica fiber and travels to the reaction chamber 71. Light from the reaction chamber is directed by the glass fibers to a blue-sensitive photodiode (UV 215 BG, Princeton EG & G Electro-Optics). The glass fibers are opaque to the light from the laser. The photodiode output is sent to the Keithley amplifier which feeds the recorder 49. This apparatus is used to determine hydrogen peroxide by a fluorescent method relying on the oxidation of para-hydroxyphenylacetic acid (PHPA) at pH 5.5 by hydrogen peroxide, catalyzed by the enzyme peroxidase, followed by the addition of base to raise the pH to above about 10 (see Hwang and Dasgupta, *Anal. Chem.* 58, 1521, 1986 for more details about this reaction). This results in a fluorescent product (wavelength of maximum excitation of 329 nm, wavelength of maximum emission of 412 nm which the glass fibers will transmit). The reagent 22 is 0.1 liter of 0.05 M pH 5.5 phosphate buffer containing 40 milligrams of Type II Sigma Chemical Co. peroxidase enzyme. The reagent 23 is 0.04 percent PHPA containing 0.6% disodium EDTA at pH 5.5. The reagent in the third reservoir is 0.5 M sodium hydroxide in water. The sample injection volume is 0.255 milliliter of hydrogen peroxide (0.25–3 millimolar). 0.088 milliliter of reagent 22 is then added to the reaction chamber 71, followed by 0.100 milliliter of reagent 23. The mixture is stirred for 30 seconds and then 0.142 milliliter of the reagent in the third reservoir is added to the chamber 71 and stirred for 10 seconds and then the stirrer is turned off and the mixture allowed to sit for 30 seconds. Then the fluorescence intensity is recorded for 5 seconds. The calibration plot is linear at hydrogen peroxide concentrations below 0.5 millimolar and exhibits a negative deviation from linearity above this, likely due to self-quenching. This example demonstrates a microbatch reaction with a fluorescencephotometric probe exposed to the reaction chamber.

What is claimed is:

1. Apparatus for automatic microbatch reaction, comprising;
    (a) a reactor defining a reaction chamber;
    (b) an automatic liquid sample injection valve in fluid communication with the reaction chamber;
    (c) means for automatically flowing a time - controlled variable-sized microvolume of a liquid reagent into the reaction chamber; and
    (d) means for supplying gas under pressure in fluid communication with the injection valve so that a preselected microvolume of sample can be blown by said gas into the reaction chamber.

2. The apparatus of claim 1 having a plurality of means for automatically flowing a time - controlled variable - sized microvolume of a liquid reagent into the reaction chamber wherein each means for automatically flowing a time - controlled variable - sized microvolume of a liquid reagent into the reaction chamber includes an on-off valve being in liquid communication with the reaction chamber, each on-off valve being automatically controlled by an automatic control means that includes a microcomputer.

3. The apparatus of claim 1, further comprising a detector valve in fluid communication with a detector and the reaction chamber near the bottom of the reaction chamber, the detector valve being automatically controlled by an automatic control means so that any liquid contents of the reaction chamber can be automatically allowed to flow to the detector.

4. The apparatus of claim 3, wherein the detector valve is a three-way valve, the three-way valve also being in fluid communication with a gas pressurizable gas valve, the gas pressurizable gas valve being automatically controlled by the automatic control means so that a time - controlled variable - sized microvolume of a liquid reagent can be flowed into the reaction chamber and therein react with a liquid sample blown into the reaction chamber, the sample and reagent mixed in the reaction chamber by gas flowing through the gas valve and the three-way valve into the reaction chamber before being automatically allowed to flow from the reaction chamber to the detector.

5. The apparatus of claim 4, further comprising a vent valve in fluid communication with the reaction chamber near the top of the reaction chamber, the vent valve being automatically controlled by the automatic control means so that the reaction chamber can be automatically vented when gas is flowing through the gas valve and the three-way valve into the reaction chamber.

6. The apparatus of claim 2 wherein the means for automatically flowing a time - controlled variable - sized microvolume of a liquid reagent into the reaction chamber includes an on-off valve being in liquid communication with the reaction chamber.

7. The apparatus of claim 6 wherein the on-off valve and the sample injection valve are automatically controlled by an automatic control means.

8. The apparatus of claim 7 wherein the automatic control means includes a microcomputer.

9. The apparatus of claim 1, further comprising a sensor exposed to the reaction chamber so that the sample can be titrated by the reagent or so that a reaction product of the sample and the reagent can be determined.

10. The apparatus of claim 9, further comprising means for mixing a liquid in the reaction 11. The apparatus of claim 10, wherein the means for mixing a liquid in the reaction chamber comprises a magnetic stirring bar positioned within the reaction chamber.

12. The apparatus of claim 11, further comprising a drain valve in fluid communication with the reaction chamber near the bottom of the reaction chamber so that any liquid in the reaction chamber can be allowed to flow out of the reaction chamber.

13. The apparatus of claim 12, wherein the sensor is selected from the group consisting of potentiometric probes, conductimetric probes, amperometric probes, and photometric probes.

14. A method for automatic microbatch reaction, comprising the steps of:
    (a) automatically flowing a preselected microvolume of a liquid sample into a reaction chamber;
    (b) automatically flowing a controlled microvolume of a liquid reagent into the reaction chamber for a length of time, the controlled microvolume being a function of the length of time;
    (c) determining the concentration of an analyte in the reaction chamber, the analyte selected from the group consisting of a component of the sample, a component of the reagent and a reaction product between a component of the sample and a component of the reagent; and (d) repeating step (b) so that another microvolume of reagent can be added to the reaction chamber.

15. A method for automatic microbatch reaction, comprising the steps of:

(a) automatically flowing a preselected microvolume of a liquid sample into a reaction chamber, the flowing being accomplished by a flowing stream of a gas to blow a preselected microvolume of liquid sample into the reaction chamber; and (b) automatically flowing a controlled microvolume of a liquid reagent into the reaction chamber for a length of time, the controlled microvolume being a function of the length of time, so that a component of the sample can react with a component of the reagent to produce a reaction product.

16. The method of claim 15, further comprising the step of determining the concentration of an analyte in the reaction chamber, the analyte selected form the group consisting of a component of the sample, a component of the reagent and a reaction product between a component of the sample and a component of the reagent.

17. The method of claim 16, wherein step (b) is repeated so that another microvolume of reagent can be added to the reaction chamber.

* * * * *